United States Patent [19]

Pastrone

[11] 4,453,931
[45] Jun. 12, 1984

[54] INTRAVENOUS METERING DEVICE

[75] Inventor: Giovanni Pastrone, Los Gatos, Calif.

[73] Assignee: Oximetrix, Inc., Mountain View, Calif.

[21] Appl. No.: 278,954

[22] Filed: Jun. 30, 1981

Related U.S. Application Data

[63] Continuation-in-part of Ser. No. 174,666, Aug. 1, 1980, Pat. No. 4,336,800.

[51] Int. Cl.³ .............................................. A61M 5/00
[52] U.S. Cl. ................................... 604/153; 604/123; 417/38; 417/443; 417/510
[58] Field of Search ........... 128/214 R, 214 E, 214 F, 128/DIG. 12, DIG. 13, 273; 417/38, 435, 443, 510, 478, 479; 604/151–153, 118, 122, 123

[56] References Cited

U.S. PATENT DOCUMENTS

| | | | |
|---|---|---|---|
| 3,543,752 | 12/1970 | Hesse et al. | 128/214 E |
| 4,126,132 | 11/1978 | Portner et al. | 128/214 F |
| 4,140,118 | 2/1979 | Jassawalla | 128/214 F |
| 4,142,524 | 3/1979 | Jassawalla et al. | 128/214 F |
| 4,236,880 | 12/1980 | Archibald | 128/214 F X |
| 4,276,004 | 6/1981 | Hahn | 417/479 |
| 4,277,227 | 7/1981 | Jenkins | 128/214 E |
| 4,303,376 | 12/1981 | Siekmann | 604/153 X |
| 4,336,800 | 6/1982 | Pastrone | 128/214 F |

Primary Examiner—Dalton L. Truluck
Attorney, Agent, or Firm—Robert S. Kelly

[57] ABSTRACT

A device for precise metering of liquids for intravenous delivery to a patient, the device including a pumping chamber with a reciprocable diaphragm positioned therein. The device also includes valves positioned at the pumping chamber inlet and outlet, the valve at the pumping chamber inlet being operated independently of the pressure within the pumping chamber. The device also includes a gas retention chamber having an upper portion providing for the formation of the gas-liquid interface and a lower portion from which liquid free of gas bubbles may be removed.

4 Claims, 5 Drawing Figures

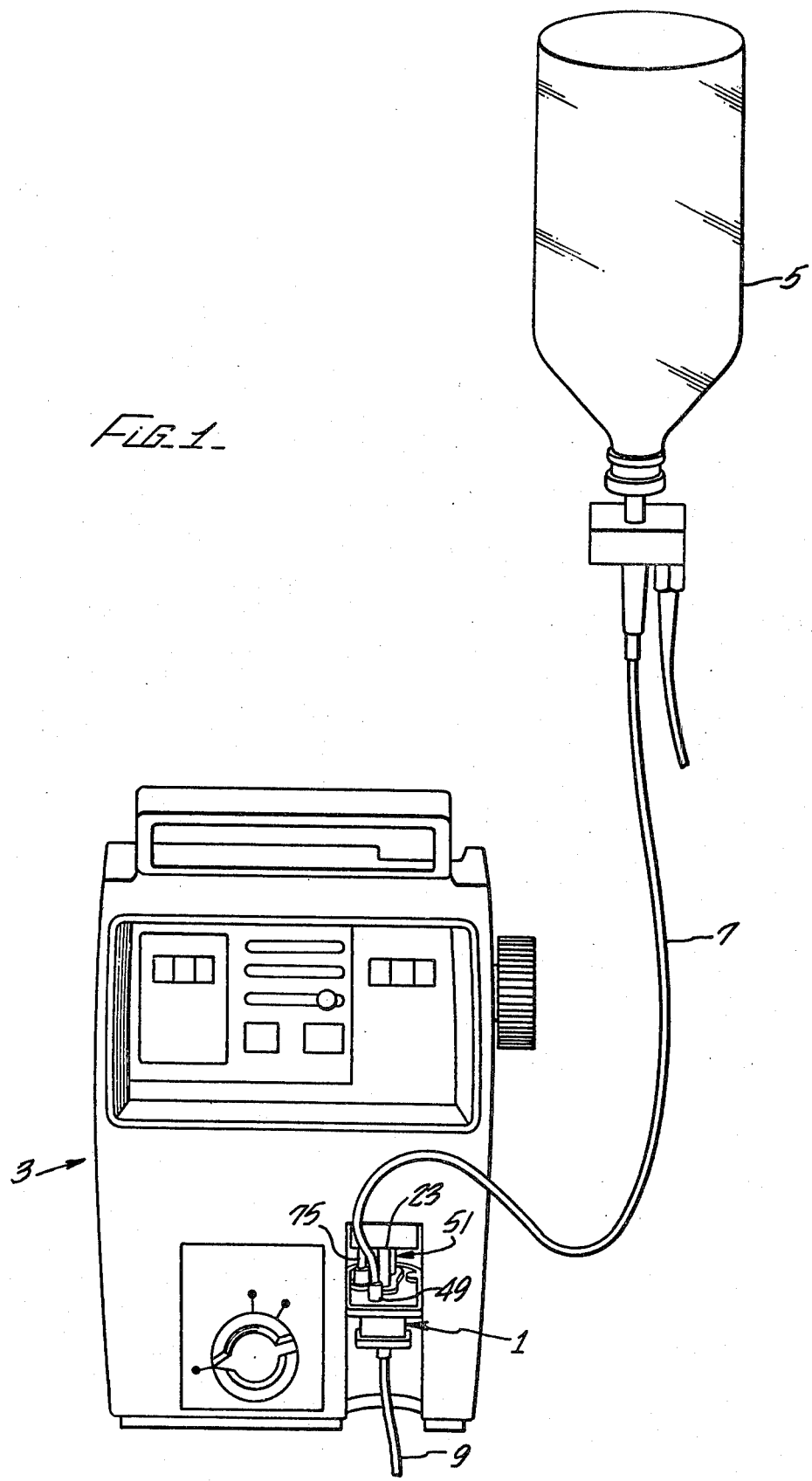

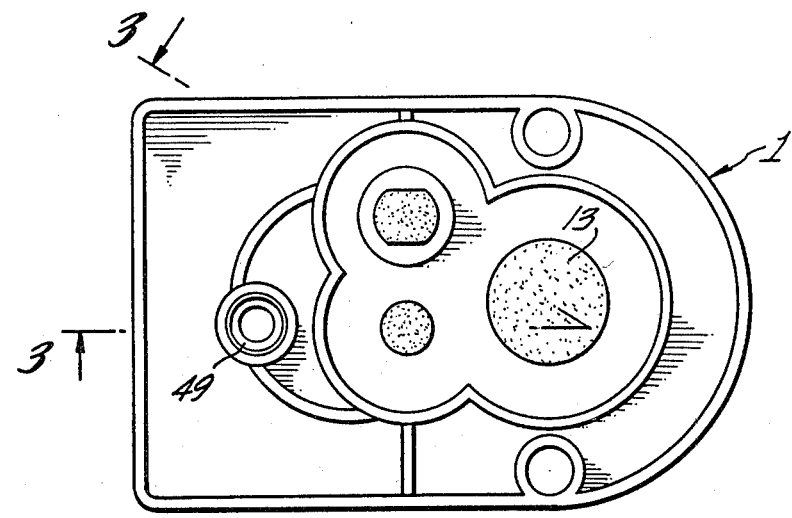
FIG_2.
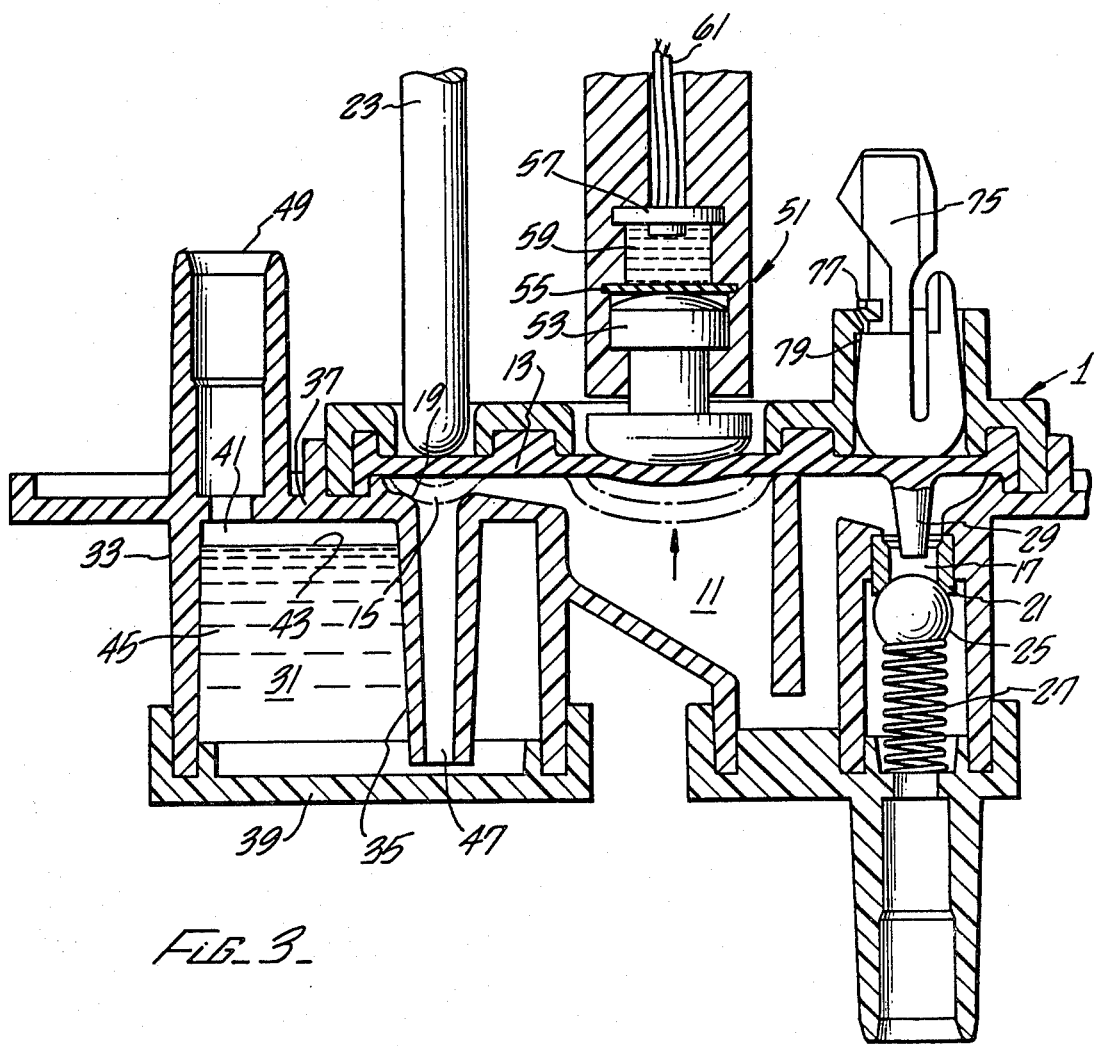
FIG_3.

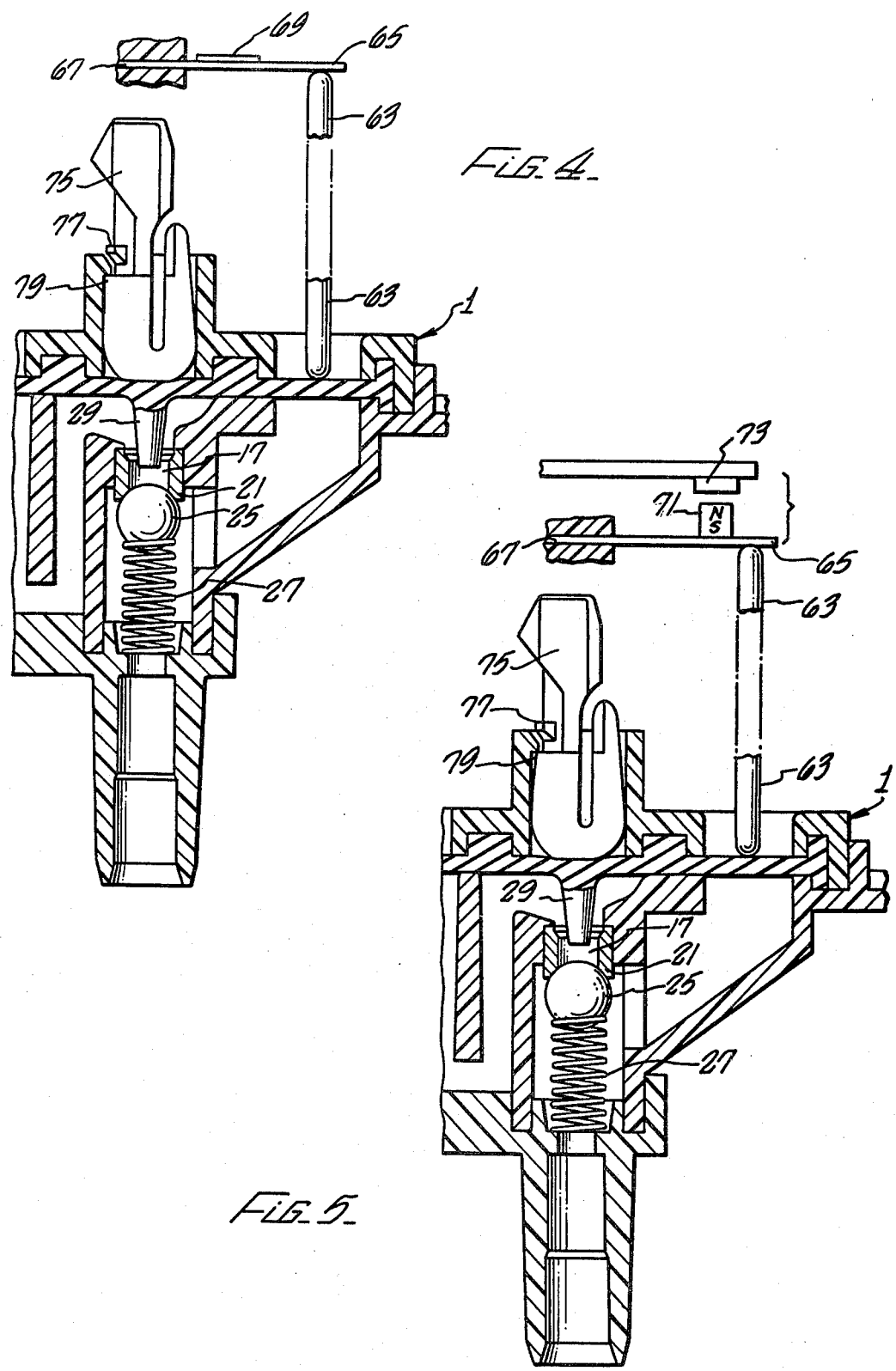

4,453,931

INTRAVENOUS METERING DEVICE

RELATED APPLICATION

This application is a continuation-in-part of my copending U.S. application Ser. No. 174,666 filed Aug. 1, 1980 and titled Intravenous Metering Device, now U.S. Pat. No. 4,336,800 issued June 29, 1982.

BACKGROUND OF THE INVENTION

Considerable attention has been directed to intravenous delivery of fluids to patients, such as saline solutions and the like, in the last several years. Initially, such materials were administered to a patient by means of gravity flow from a container containing the liquid to be delivered. A difficulty encountered with such devices was that administration by gravity flow often required that the container for the liquid to be transmitted to the patient had to be positioned at a considerable elevation above the patient. Further, attempts to accurately regulate the flow of such devices proved difficult because of the fact that the pressure causing the flow of the liquid to the patient decreased as the liquid level within the container was reduced during the delivery operation.

SUMMARY OF THE INVENTION

With the intravenous metering device of the present invention an infusion pump is provided which is of the conventional gas-disabling type, i.e., one which will not pump liquid if there is any appreciable amount of air in the pumping chamber. The device of the present invention is capable of consistently pumping precise amounts of liquid to the patient—an obvious advantage in I.V. therapy.

Thus, the device of the present invention includes a rigid shell forming a pumping chamber having an inlet and an outlet. The outlet is closed by a valve which is biased into the closed position by a predetermined pressure. Liquid is pumped by a piston-type pumping means which is reciprocated so as to periodically extend into the chamber to decrease the volume thereof thus raising the pressure therein to overcome the biasing pressure on the outlet valve permitting an amount of liquid to be discharged equal to the pumping chamber volume occupied by the pumping means in its fully extended position. The inlet valve is provided by a resilient diaphragm which extends over an opening in the pumping chamber shell and which can be moved by an external actuator member into an extended position so as to seal the inlet to the pumping chamber. Thus, such actuator member can be moved so as to close the inlet prior to the movement of the pumping means in its pumping stroke and will remain closed during the entire inwardly extending movement of the pumping means. Afterwards, the actuator member can be retracted to permit the resilient diaphragm to retract from the chamber inlet thereby permitting the refilling of the chamber with liquid.

DRAWINGS

FIG. 1 is a pictorial view illustrating the use of the present invention.

FIG. 2 is a top plan view of one embodiment of the device of the present invention.

FIG. 3 is a reduced cross-sectional view taken about 3—3 of FIG. 2.

FIGS. 4 and 5 are partial cross-sectional views illustrating different embodiments of the device of the present invention.

DESCRIPTION OF PREFERRED EMBODIMENTS

Referring now to FIG. 1, the intravenous metering device 1 is shown positioned within a metering device control unit 3. The intravenous metering device 1 is connected to a container of fluid 5 by means of conventional tubing 7. Tubing 9, extending from the outlet of the intravenous metering device 1 transfers precise amounts of fluid to the patient to be treated.

Referring now to FIGS. 2 and 3 the construction of the intravenous metering device 1 of the present invention will be discussed in detail. The intravenous metering device 1 includes a rigid shell forming pumping chamber 11 and a reciprocable diaphragm 13 which forms the upper wall of the pumping chamber 11. The intravenous metering device 1 includes a pumping chamber inlet 15 and a pumping chamber outlet 17. Pumping chamber inlet 15 includes a valve seat means 19. Similarly, pumping chamber outlet 17 includes valve seat means 21. Valve actuator 23 controls the admission of fluid into the pumping chamber 11 by reciprocating between the open position, shown by the solid line position of diaphragm 13 in FIG. 3 and the closed position 1, shown by the dotted line position of diaphragm 13 at the inlet 15 in FIG. 3. A ball check valve 25 is positioned such that it is normally in a position so as to seat against valve seat means 21 of pumping chamber outlet 17. The ball check valve 25 is normally held in the closed position by biasing means spring 27.

The reciprocable diaphragm 13 includes a projection 29 opposite ball check valve 25. The cross-sectional area of the liquid flow path through the pumping chamber 11 is approximately equal to the cross-sectional area of the pumping chamber inlet 15 and the pumping chamber outlet 17. One of the advantages of this relationship is the relatively constant, high velocities of fluid flow experienced during the filling operation of the intravenous metering device 1.

The rigid shell of intravenous metering device 1 further includes a gas retention chamber 31 bounded by a sidewall 33 and opposed walls 37 and 39. As shown in FIG. 3, the gas retention chamber 31 includes a gas retaining upper portion 41, providing for a gas-liquid interface 43, and a lower portion 45 from whence liquid free of gas bubbles may pass from the gas retention chamber lower portion 45 through a gas retention chamber passageway 47 and into the pumping chamber 11. The passageway 47 is formed within a tapered tube 35 extending from a position spaced just above bottom wall 39 to a position spaced just below the diaphragm 13. It will be noted that the upper portion of tube 35 forms the valve seat means 19 at the pumping chamber inlet 15. An upstanding inlet tube 49 is positioned on the upper wall 37 of the gas retention chamber and is adapted to receive the tubing 7 carrying the incoming liquid.

It is desirable to measure the discharge pressure of the intravenous metering device 1. Excessive back pressure may indicate a plugged filter or discharge line occlusion, etc. which requires correction. Accordngly, the intravenous metering device 1 includes pressure indicating device for determining the discharge pressure. FIG. 3 illustrates a pumping piston 51 which reciprocates against the flexible diaphragm 13 and thereby pumps liquid free of gas bubbles through the intravenous metering device 1. The relaxed position of the diaphragm 13 shown by solid lines in FIG. 3 is obtained when the pumping piston 51 is in the upstroke position (as shown) while the dashed line indication of the diaphragm below the pumping piston 51 is obtained when the piston is in the downstroke position. Positioned within pumping piston 51 is an internal piston head 53 which is forced upward against internal diaphragm member 55 during the downstroke of pumping piston 51 due to the increasing pressure produced in the pumping chamber 11. This force exerted on the diaphragm member 55 by the internal piston, head 53 is in turn, measured by pressure transducer 57 suspended within a fluid medium 59, preferably a silicon gel, and then transmitted in converted form to an external pressure read out through electrical leads 61.

Alternately, as shown in FIGS. 4 and 5, a separate opening can be provided in the shell forming the upper wall of the metering device 1 which opening is covered by the resilient diaphragm 13. The opening leads to a passage extending into the body of the device and opening into the discharge passage of the device just downstream of the pumping chamber outlet 17, as shown in FIGS. 4 and 5. A discharge pressure pin 63 is positioned above and in contact with the diaphragm 13 whereby the diaphragm will be forced upward against the discharge pressure pin 63 as the discharge pressure increases. The resultant upward movement of discharge pressure pin 63, in turn, produces movement of a flexure beam 65 anchored at one end at 67. This movement may then be translated into a pressure read out through employment of a conventional strain gage 69 (as shown in FIG. 4) or the combination of a magnet 71 and a Hall Effect Device 73 which measures the change in electron flow as the magnetic field about the Hall Effect Device 73 is altered by movement of magnet 71 with respect to the Hall Effect Device 73 (as shown in FIG. 5). For a more detailed explanation of Hall Effect Devices see "Hall Effect Devices and Their Applications", *Electronics Industry*, May 1979, pp. 21-17.

The detailed construction of the intravenous metering device 1 of this invention having been described, its method of operation will now be discussed. Incoming fluid, transmitted by tubing 7 to the intravenous metering device inlet tube 49 passes into the gas retention chamber 31 which, due to the extension of pumping chamber inlet tube 35 to near the bottom of the gas retention chamber prevents any gases therein from entering the pumping chamber 11. The size and shape of the gas retention chamber allows for the generation of a gas-liquid interface 43 at the gas retention chamber upper portion 41. Liquid free of gas bubbles passes from the gas retention chamber lower portion 45 through gas retention chamber passageway 47. When the valve actuator 6 is reciprocated upwardly, liquid free of gas bubbles is allowed to pass into pumping chamber 11. Valve actuator 61 is then closed. As the reciprocable diaphragm 13 is reciprocated downwardly by means of the pumping piston 51, the volume within the pumping chamber 11 is decreased and the pressure within the pumping chamber 11 overcomes the force of the spring biasing 27 urging pumping chamber outlet ball check valve 25 to become disengaged from pumping chamber outlet valve seat means 21 thereby allowing a precise amount of metered fluid to be pumped from the pumping chamber 11 through the intravenous metering device outlet to a patient by means of tubing 9. The intravenous metering device 1 of the present invention may be disposable such that a fresh and sterilized intravenous metering device 1 is employed at each application of intravenous passage of fluid to a patient.

When the device is to be filled, a manual latch valve 75 (FIGS. 3-5) is depressed such that stop 77 thereon engages shoulder 79 of the body of the intravenous metering device 1 thereby forcing diaphragm projection 29 into contact with ball check valve 25 compressing spring 27 so as to allow for filling liquid to pass through the pumping chamber outlet 17 and fill the outlet tubing 9.

The present device is to be contrasted with those prior art intravenous metering devices using internal valves which close only under a higher pressure in the pumping chamber than exists upstream therefrom. In such devices, it is the decrease in pressure within the pumping chamber which opens the inlet valve, and conversely, an increase in pressure within the pumping chamber of such devices closes the inlet valve.

Because the valve actuator 23 admits liquid free of gas bubbles into the pumping chamber 11 prior to the pumping stroke of pumping piston 51, independent of the pressure within the chamber 11, the pumping piston 51 of the present invention produces a more carefully measured precise amount of fluid than that of the aforedescribed prior art devices using internal pressure controlled valves. Such devices, during the initial pumping stroke, pump liquid backward and out the inlet until a sufficient pressure is reached necessary to close the inlet valve. In the present invention there is no backward flow out through the pumping chamber inlet.

It is obvious that certain changes can be made to the preferred form of the invention as described above. Accordingly, the claims should be given an interpretation commensurate with the scope of the invention as set out in the claims appended hereto.

What is claimed is:

1. A device for the precise metering of liquids for intravenous delivery to a patient, said device comprising a substantially rigid shell forming a pumping chamber, said chamber having an upper wall with first, second and third openings therein, a first resilient diaphragm covering said first opening and being adapted to be selectively engaged by an actuator member to move it from a relaxed position to a stressed position extending into the pumping chamber, means forming an inlet port for admitting liquid into said pumping chamber, said inlet port being positioned generally parallel to and closely spaced from said diaphragm in its relaxed position so that when said diaphragm is moved into its stressed position by said actuator member it will seal said inlet port to prevent the flow of liquid therethrough, said chamber having an outlet port spaced below the inlet port for the discharge of liquid from the chamber, an outlet valve for closing said outlet port including means for biasing said valve in its closed position with a predetermined biasing pressure, a second resilient diaphragm positioned to cover said second opening in said wall and adapted to be engaged by a piston to cause it to be extended into said chamber to create a pressure within the chamber capable of overcoming the biasing pressure to permit the discharge of liquid from the chamber, and a third diaphragm covering the third opening and having a projecting portion depending therefrom, said third opening being located above said outlet port whereby a projection member may be arranged to engage said third diaphragm within said third opening to cause the projecting portion thereof to engage the outlet valve to open said outlet port and permit the filling of the device and the tubing downstream thereof with liquid.

2. A device according to claim 1 wherein said upper wall includes a fourth opening covered by a fourth diaphragm, said shell having a passage extending from said fourth opening to a fluid passage downstream of said outlet port, said fourth diaphragm covering the fourth opening being adapted to be engaged by a pressure sensor to continuously monitor the liquid pressure between the device and the patient as reflected by said fourth diaphragm.

3. A device according to claim 1 wherein said first, second and third diaphragms are comprised of a single member, and means for fixedly securing the diaphragm member to the upper wall between each of said openings.

4. A device according to claim 2 wherein said first, second, third and fourth diaphragms are comprised of a single member, and means for fixedly securing the diaphragm member to the upper wall between each of said openings.

* * * * *